2/11/86 XP 4,569,840

United States Patent [19]

Kit

[11] Patent Number: 4,569,840

[45] Date of Patent: Feb. 11, 1986

[54] THYMIDINE KINASE-NEGATIVE TEMPERATURE RESISTANT BOVINE HERPESVIRUS-1 MUTANT AS A VACCINE AGAINST INFECTIOUS BOVINE RHINOTRACHEITIS

[75] Inventor: Saul Kit, Houston, Tex.

[73] Assignees: Baylor College of Medicine; NovaGene, Ltd., both of Houston, Tex.

[21] Appl. No.: 516,179

[22] Filed: Jul. 21, 1983

[30] Foreign Application Priority Data

Feb. 25, 1983 [GB] United Kingdom ................ 8305323

[51] Int. Cl.[4] ........................ A61K 39/12; C12N 7/06

[52] U.S. Cl. ........................................ 424/89; 435/238

[58] Field of Search .................. 424/89; 435/235-237, 435/172.1, 240

[56] References Cited

U.S. PATENT DOCUMENTS

| | | | |
|---|---|---|---|
| 3,876,764 | 4/1975 | Straub | 424/89 |
| 3,907,986 | 9/1975 | Zygraich et al. | 424/89 |
| 4,132,775 | 1/1979 | Volenec et al. | 424/89 |
| 4,282,210 | 8/1981 | Irwin | 424/89 |
| 4,291,019 | 9/1981 | Lupton et al. | 424/89 |
| 4,322,404 | 3/1982 | Gauri et al. | 424/89 |
| 4,514,497 | 4/1985 | Kit et al. | 424/89 X |

OTHER PUBLICATIONS

Kit S., et al., *Virology* 85, 456–463 (1978).
Schaffer et al., Virology 42, 1144–1146 (1970).
Field, H. J. et al., *J. Hyg. Camb.*, (1978), 81, 267.
Weinmaster G. A., et al., *Virology* 118, 191–201 (1982).
Kit, S. et al., *Virology* 130, 381-389 (1983).
Shiraki et al., Biken Journal, vol. 26, 17–23 (1983).
Kit et al., Virology, 76, 331-340 (1977).
Matz et al., J. Gen. Vir., 64, 2261-2270, 1983.
Fenner et al., *The Biology of Animal Viruses*, 2nd Ed., Academic Press, N.Y., 1974, pp. 276-287.
Subak-Sharpe et al., in Cold Spring Harbor Symposia on Quantitative Biology, vol. XXXIX, Tumor Viruses, 717-730, Cold Spr. Harbor Lab., 1975.
Misra et al., Archives of Virology, 76, 341-354 (1983).
Engels et al., Archives of Virology, 67, 169-174 (1981).
Kendrick et al., The Cornell Vet., vol. XLVIII, No. 4, 458–495, Oct. 1958.
Ludwig et al., Med. Microbiol. Immunol., 158, 209-217 (1973).
Kendrick, J.A.V.M.A., vol. 163, No. 7, 852-854.
Allen et al., Virology 90, 351-359 (1978).
Benyesh-Melnick et al. in *Cold Spring Harbor Symposia on Quantitative Biology*, vol. XXXIX, Tumor Viruses, Cold Spring Harbor Laboratory, 1975.

*Primary Examiner*—Esther M. Kepplinger
*Assistant Examiner*—Shawn P. Foley
*Attorney, Agent, or Firm*—Sughrue, Mion, Zinn, Macpeak, and Seas

[57] ABSTRACT

Described are thymidine kinase negative temperature resistant mutants of bovine herpesvirus effective in inducing resistance to infectious bovine rhinotracheitis, methods for their production, methods for maintaining them in viable form, and methods for administering them to animals in immunologically effective doses to induce resistance to infectious bovine rhinotracheitis.

17 Claims, No Drawings

THYMIDINE KINASE-NEGATIVE TEMPERATURE RESISTANT BOVINE HERPESVIRUS-1 MUTANT AS A VACCINE AGAINST INFECTIOUS BOVINE RHINOTRACHEITIS

BACKGROUND OF THE INVENTION

Bovine herpesvirus type 1 (BHV-1) causes infectious bovine rhinotracheitis, a highly contagious disease of cattle, characterized by severe inflammation of the upper respiratory passages and trachea. This virus is also an etiologic agent of vulvovaginitis, balanoposthitis, abortion, conjunctivitis, meningoencephalitis, and fatal systemic infections. Lupton and Reed, *Evaluation of Experimental Subunit Vaccines for Infectious Bovine Rhinotracheitis,* Am. J. Vet. Res. 41, 383–90 (1980). Natural infections have been described in cattle, goats, swine, water buffalo, wildebeests, and ferrets. Experimental infections have been established in mule deer, goats, swine, ferrets and rabbits. Fulton et al., *Prevalence of Bovine Herpes Virus-*1, *Bovine Viral Diarrhea, Parainfluenza-*3, *Bovine Adenoviruses-*3 *and -*7, *and Goat Respiratory Syncythial Viral Antibody in Goats,* Am. J. Vet. Res. 43, 1454–57 (1982). Infected cattle may have temperatures ranging from 104° to 107° F., a heavy mucous nasal discharge, depression, loss of appetite, increased rate of respiration, labored breathing, and coughing. Superinfection by *Pasturella haemolytica* often results in severe pneumonia.

The severity of the illness resulting from BHV-1 infection depends upon the virus strain and on the age of the animal affected. Encephalitis and death are generally restricted to calves. After recovery from BHV-1 infection, animals may show clinical signs of recurrent disease without being reexposed to the virus. Recurrent disease without reexposure occurs because the virus remains dormant in the neurons of the sensory ganglia of its host and can be reactivated even after long periods. Dexamethasone treatment can provoke release of the virus from the neurons and viral shedding with or without clinical signs and symptoms of active BHV-1 disease. Ackermann, et. al., *DNA of Bovine Herpes Virus Type* 1 *in the Trigeminal Ganglia of Latently-Infected Calves,* Am. J. Vet. Med., 43, 36–40 (1982). Additionally, stress caused by transportation or parturition often causes reactivation of latent BHV-1 in infected calves.

Infections caused by BHV-1 were first recognized in the United States in the mid-1950's. These infections had, however, existed in Europe for at least one hundred years and had been described scientifically in 1928. By the mid-1960's, respiratory disease caused by BHV-1 was causing losses in the United States estimated at $25 million. Additional losses associated with BHV-1 infections resulted from abortion storms, dramatic losses in milk yield, fatal metritis, enteritis, and meningitis. Since 1972, more severe forms of BHV-1 respiratory infections have become widespread in Western Europe and Canada. The increased infection severity suggests emergence of more virulent BHV-1 strains. New infectious bovine rhinotracheitis outbreaks probably result from exposure to imported asymptomatic BHV-1 carriers or exposure to infected animals prior to onset of clinical disease.

Currently, three types of infectious bovine rhinotracheitis vaccines are available: inactivated adjuvant vaccines, subunit vaccines, and modified live virus (MLV) vaccines. Inactivated BHV-1 vaccines are produced by treating the virus with formalin or ethanol and heat or by ultraviolet irradiation. Subunit BHV-1 vaccines are prepared by solublizing BHV-1 infected cell cultures with nonionic detergents. The early modified live virus vaccines were designed for parenteral administration and consisted of virus attenuated by rapid passage in bovine cell cultures. Schwartz, et al., *Modification of Infectious Bovine Rhinotracheitis* (*IBR*) *Virus in Tissue Culture and Development of a Vaccine,* Proc. Soc. Exp. Biol. Med. 96,453–58 (1957). Subsequent parenterally administered MLV vaccines were attenuated by adaptation of the virus to porcine or canine cell cultures, adaptation to growth and cell culture at 30° C., or by selection of heat-stable mutants (56° C. for 40 minutes). The presently available MLV vaccines are administered intranasally and are attenuated by serial passage in rabbit cell cultures or by treatment of the virus with nitrous acid followed by selection of temperature-sensitive mutants, that is, viruses that replicate efficiently at about 33°–37° C., but not at 39° C. *Vaccine Preparation Techniques,* Ed. by J. I. Duffy, Noyes Data Corporation, Parkridge, N.J. 1980, pp. 98–102; Lloyd-Evans, L. P., "*Tracherine.*" *Infectious bovine rhinotracheitis vaccine. Temperature-specific IBR virus strain RLB* 106 *ts.* produced by the Technical Services Department, Smith Kline Animal Health Ltd., Welwyn Garden City, Hertfordshire, United Kingdom, 1979, pp. 1–78.

Each of the available types of infectious bovine rhinotracheitis vaccines has, however, proved unsatisfactory in commercial use. Inactivated adjuvant vaccines are undependable and inadequately protective and generally inferior to MVL vaccines. For example, an inactivated virus vaccine with a 5-component adjuvant was found entirely ineffective in producing immunity, preventing disease, and suppressing propagation and reexcretion of virulent virus. Msolla, et. al., *Vaccination Against Infectious Bovine Rhinotracheitis,* Vet. Record 104, 535–36 (1979). Following challenge exposure to virulent virus, vaccinated animals exhibited clinical signs and virus excretion responses virtually identical to unvaccinated animals and, in marked contrast to calves recovered from natural infection, transmitted virulent virus to in-contact controls. The lack of efficacy of inactivated virus vaccines has also been demonstrated by inducing tracheitis, tachypnea, pyrexia, occular and nasal discharges, and severe ulceration of the nasal mucosa by exposing animals previously vaccinated with an inactivated polyvalent vaccine to BHV-1 virus.

Extensive utilization of modified live virus vaccines has reduced the frequency of infectious bovine rhinotracheitis. However, none of the available modified live virus vaccines is entirely satisfactory for use in infectious bovine rhinotracheitis control programs. For example, bovine kidney passaged Colorado Strain BHV-1 modified live virus vaccine was administered to calves intravenously, intrapreputially, or intranasally. Sheffy and Rodman, *Activation of Latent Infectious Bovine Rhinotracheitis,* J. Am. Vet. Med. Assoc. 163, 850–51, (1973). Beginning ten weeks after vaccination, dexamthasone was administered to some of the calves to induce release of latent virus. In dexamethasone treated calves, BHV-1 was found in the respiratory and genital tract tissues of intrapreputially and intravenously vaccinated calves and the respiratory tract tissues of intranasally vaccinated calves. BHV-1 virus was not found in unvaccinated calves. These data, therefore, clearly demonstrate that latent BHV-1 infections resulted from innoculation with the modified live virus vaccine. Because stress can also cause release of latent virus, prevention of latent infections is important to avoid spread of pathogenic virus and disease to non-vaccinated cattle.

Vaccination with available modified live virus preparations is also ineffective in preventing latent infection following exposure to virulent BHV-1. To demonstrate this inefficacy, a modified live virus vaccine, obtained by passing BHV-1 forty-three times in porcine testes cells followed by eight passages in monolayer cultures of bovine testes at 30° C. was employed. Narita, et al., *Neural Changes in Vaccinated Calves Challenge Exposed With Virulent Infectious Bovine Rhinotracheitis Virus*, Am. J. Vet. Res. 41, 1995-99 (1980). Following vaccination, the calves were challenge exposed to virulent BHV-1 (Los Angeles Strain). Latent viral infection was demonstrated by administering dexamethasone forty-nine days following the challenge exposure and observing signs of recurrent infection. Calves vaccinated with a temperature-sensitive intranasal vaccine were also incompletely protected against latent viral infection following exposure to virulent virus. Rossi and Kiesel, *Effect of Infectious Bovine Rhinotracheitis Virus on Virus Shedding in Challenge Exposed Calves Treated With Dexamethasone*, Am. J. Vet. Res. 43, 1576-79 (1982).

In addition to the demonstrated inefficacy in preventing latent viral infections, available modified live virus vaccines often fail to prevent active disease. Cattle have developed respiratory tract disease and conjunctivitis following modified live virus vaccination. Also, periodic shedding of BHV-1 and development of mild clinical symptoms have been described after intranasal vaccination of cattle with modified live virus vaccine. Actively infected cattle and those shedding virus create a danger of disease transmission when these cattle come into contact with non-vaccinated animals.

The presently invented modified live virus vaccine, utilizing a BHV-1 mutant that is thymidine kinase negative (TK$^-$) and temperature resistant (tr), overcomes many of the problems that have limited the use of currently available vaccines. This mutant lacks the ability to induce thymidine kinase activity in cells it infects and it can replicate efficiently in cells at 39° C. These characteristics directly contribute to its superiority as a vaccine. Virus encoded thymidine kinase activity is important for BHV-1 virulence, for replication in nerve cells which lack inherent thymidine kinase activity, and for recrudescense. This mutant provides a stronger immunologic response than temperature sensitive mutants because its resistance to elevated temperatures allows it to replicate efficiently in tissues deep within the body and in febrile animals. Intranasal administration of the TK$^-$tr BHV-1 mutant in calves does not result in symptoms of active infectious bovine rhinotracheitis disease. Further, it is now well-established that TK$^-$herpes viruses mutliply poorly in nerve cells and are less likely to cause latent infection. It is also difficult to reactivate TK$^-$tr herpes viruses and they do not recrudesce. Yet, vaccines utilizing these mutants are highly effective in preventing infection by virulent BHV-1. Additionally, vaccination with these mutants protects against latent infection development following exposure to virulent virus. Field & Wildy, *The Pathogenicity of Thymidine Kinase-Deficient Mutants of Herpes Simplex Virus in Mice*, J. Hygiene (Cambridge) 81-267-77 (1978); Field & Darby, *Pathogenicity in Mice of Strains of Herpes Simplex Virus Which Are Resistant To Acyclovir In Vitro and In Vivo*, antimicrobial agents and chemotherapy 17, 209-16 (1980); Tenser, et al., *Trigeminal Ganglion Infection by Thymidine Kinase-Negative Herpes Simplex Virus*, Science 205, 915-17 (1979).

PRIOR ART STATEMENT

Applicants are unaware of any prior art teaching the production and isolation of thymidine kinase negative, temperature-resistant bovine herpesvirus mutants (TK$^-$tr BHV-1) effective in inducing resistance to infectious bovine rhinotracheitis, the formation of working TK$^-$tr BHV-1 virus pools by propagation in cultured rabbit skin (RAB-9) fibroblasts, or the use of TK$^-$tr BHV-1 in animals to induce resistance to infectious bovine rhinotracheitis virus infections.

Prior art teaches a method of isolating thymidine kinase negative bovine herpesviruses by propagation in media containing bromovinyldeoxyuridine (BVDU). Weinmaster, et al., *Bovid Herpesvirus Type 1 (Infectious Bovine Rhinotracheitis Virus)-Induced Thymidine Kinase*, Virology 118, 191-201 (1982). However, the rationale for using bromovinyldeoxyuridine and the characteristics of the isolated virus are quite different from the rationale supporting and the virus produced by the present invention. Unlike bromodeoxyuridine, BVDU is not known to be a potent mutagen; BVDU is useful primarily for isolating spontaneously occuring TK$^-$BHV-1 mutants. In contrast, in addition to its efficacy in isolating spontaneously occuring TK$^-$BHV-1, because BrdUrd is recognized to be a potent mutagen, it is also very effective in producing multiple alterations in the viral DNA, especially those required to eliminate the virus' ability to induce thymidine kinase activity in infected cells. Therefore, the present invention goes beyond methods limited to merely isolating naturally occuring mutants and teaches a method for producing and isolating the desired mutants. The present invention also differs from the method using BVDU in that the mutants produced by this invention must be able to withstand conditions much more adverse to survival. In the present invention, the mutants are grown in cells that have inherent thymidine kinase activity. Thymidine kinase is capable of transforming BrdUrd into an agent that is toxic to BHV-1, including most TK$^-$BHV-1. Therefore, survival required the presently invented mutants to acquire resistance to the transformed BrdUrd in addition to becoming thymidine kinase negative. The use of arabinosylthymine, an agent toxic in the presence of viral encoded thymidine kinase, further insured that the mutants produced had lost the ability to induce thymidine kinase activity. Unlike the mutants isolated using BVDU, to survive these harsh conditions, the presently invented mutants had to undergo multiple genetic changes.

In addition to differences in the number of genetic changes required, the presently invented TK$^-$tr BHV-1 mutant differs from that isolated using BVDU in the extent to which it has been characterized and reduced to practice as a vaccine. Applicants have demonstrated that the presently invented mutant is capable of growing at temperatures of up to 39° C., thus increasing its efficacy as a vaccine. The temperature sensitivity of the mutant isolated using BVDU is unknown. Applicants have also shown that the presently invented TK$^-$tr BHV-1 mutant is not pathogenic in calves and is highly effective in immunizing calves against infectious bovine rhinotracheitis. No studies of the pathogenicity or immunogenicity in calves of the TK⁻BHV-1 isolated using BVDU have yet been described.

The prior art also contains examples of using various other forms of herpesvirus as a vaccine. U.S. Pat. No. 4,225,582 is directed to the use of live bovine herpesvirus in horses to confer immunity to infection by equid herpesvirus type 1. U.S. Pat. No. 4,322,404 describes a method for producing non-specific mutants of human herpes simplex virus type 1 or type 2 in two steps with phosphonoformic acid and 5-ethyl-2' desoxyruridine and then administering these mutants to mice to induce resistance to herpes simplex virus infections in mice. The following U.S. patents disclose methods of controlling infectious bovine rhinotracheitis that do not involve vaccination of animals with chemically induced mutants of BHV-1: Nos. 3,876,764; 3,907,986; 4,132,775; 4,282,210; 4,291,019.

SUMMARY OF THE INVENTION

The present invention is directed to thymidine kinase negative, temperature-resistant mutants of BHV-1 effective in inducing resistance to infectious bovine rhinotracheitis, methods of producing the mutants, including growth in media containing mutagen effective in producing the mutant and selecting for the mutant, methods of producing working pools of the mutants by propagation in cells in culture, and use of the mutants in animals as a vaccine to confer immunity to BHV-1 infections.

Accordingly, it is an object of the present invention to provide TK⁻tr mutants of BHV-1 effective in inducing resistance to infectious bovine rhinotracheitis.

A further object of the present invention is the provision of a method for producing the TK⁻tr BHV-1 mutants by growing BHV-1 under stringently adverse conditions in media containing mutagen effective in producing the mutants.

A further object of the present invention is the establishment of working pools of TK⁻tr BHV-1 by propagation in RAB-9 cells in culture.

A further object of the invention is the use of TK⁻tr BHV-1 mutants to induce resistance in animals to BHV-1 infections.

Other and further objects, features and advantages appear throughout.

DESCRIPTION OF THE PREFERRED EMBODIMENTS

Production of Thymidine Kinase Negative Temperature Resistant BHV-1 Mutants From Thymidine Kinase Positive BHV-1 Parents The following organisms are available from permanent collection of the American Type Culture Collection, 12301 Parklawn Dr. Rockville, Md., 20852, U.S.A.

ATCC VR2066: Bovine Herpesvirus type 1 (strain KIT)

The deposit is available to the public upon a grant of a patent to the Assignee, Baylor College of Medicine, disclosing them. It should be understood, however, that the availability of a deposit does not constitute a license to practice the subject inventions in derogation of patent rights granted by governmental action.

The present invention is directed to TK⁻tr BHV-1 mutants effective in inducing resistance to infectious bovine rhinotracheitis, methods of producing these mutants, and methods of confering resistance to BHV-1 infections upon animals by administering immunologically effective amounts of these mutants as vaccines.

The modified live virus vaccine comprises TK⁻tr BHV-1 mutant effective to provide resistance to BHV-1 infections that does not increase cellular thymidine kinase activity over the basal level or cause the infected cells to synthesize a virus encoded functional thymidine kinase enzyme.

The method of producing the TK⁻tr BHV-1 mutants comprises multiple passages of TK⁺ BHV-1 through cultured cells in media containing mutagen effective to produce the TK⁻tr BHV-1 mutant and then purifying the TK⁻tr BHV-1 mutants produced. Working pools of TK⁻tr BHV-1 mutants are established to maintain the mutants in viable form.

Presently Preferred Method of Producing and Isolating TK⁻tr BHV-1 Mutants

A presently preferred method of producing these TK⁻tr BHV-1 mutants is as follows:

(1) Thymidine kinase-positive rabbit skin (RAB-9) fibroblasts in culture were infected with parental thymidine kinase positive (TK⁺) BHV-1 (Los Angeles Strain) 0.01 Plaque Forming Units (PFU) per cell in media containing 10% lamb serum (range 2.5–15%) and 5-bromodeoxyuridine (BrdUrd) 5 $\mu$g/ml. and maintained at 34.5° C. in a carbon dioxide incubator for two days.

(2) The BHV-1 was then harvested and again passaged in RAB-9 cells as in step number one.

(3) The BHV-1 was then harvested and passaged in RAB-9 cells, as in step number one, except that the BrdUrd concentration was increased to 10 $\mu$g/ml.

(b 4) The BHV-1 was then harvested and plaque-purified by:

(a) infecting RAB-9 cell cultures with 0.1 ml. of BHV-1 serially diluted ($10^{-3}$ to $10^{-6}$) in media containing 10% lamb serum;

(b) allowing one hour for virus absorption at 37° C.;

(c) removing the BHV-1 innoculum and replacing it with overlay medium consisting of Eagle's minimal essential medium (APMEM), 0.04% protamine sulfate, mycostatin (50 $\mu$/ml.), neomycin, (50 mEq/ml.), 1% agar, 7.5% lamb serum, and BrdUrd 10 $\mu$g/ml. maintained at pH 7 with 0.01 M Hepes (hydroxyethylpiperazine-ethane-sulfonic acid) buffer;

(d) incubating the above for three to five days at 34.5° C.;

(e) staining the BHV-1 infected RAB-9 cells with neutral red; and (f) removing BHV-1 plaques in 0.25 ml. APMEM plus 5% lamb serum from cell culture dishes infected with $10^{-5}$ BHV-1 dilution.

(5) The removed BHV-1 was then propagated in RAB-9 cells in media containing APMEM, 10% lamb serum and BrdUrd 25 $\mu$g/ml.

(6) The BHV-1 was then harvested and plaque-purified as in step number four.

(7) A 1:100 dilution of this virus was then used to infect RAB-9 cultured cells and allowed to propagate at 34.5° C. in growth medium containing arabinosylthymine (ara-T), a thymidine analogue, 200 $\mu$g/ml.

(8) A 1:100 dilution of this virus was then passaged three times in RAB-9 cells maintained at 34.5° C. in the presence of ara-T 200 $\mu$g/ml.

(9) The BHV-1 was then passaged in RAB-9 cells at 34.5° C. in media containing APMEM, 10% lamb serum and BrdUrd 50 $\mu$g/ml.

(10) The BHV-1 was then harvested and again plaque-purified as in step number four.

To select for TK⁻tr BHV-1 mutants, portions of each of the plaque-purified viruses were used to infect duplicate cultures of RAB-9 cells growing in APMEM plus 10% fetal calf serum. One of the duplicate infected cultures was then incubated for 2 days at 34.5° C. and the other at 39.1° C. The dishes containing cells that had been incubated at 39.1° C. were stained with 0.1% crystal violet to verify that extensive virus replication had occurred at 39.1° C. and that microplaques had been produced. Virus was harvested from the duplicate dish which had been incubated at 34.5° C. Virus titrations were then carried out. The results demonstrated that the virus titers were as high at 39.1° C. as at 34.5° C. and, hence, that this BHV-1 strain was tr. By contrast, ts virus strains exhibit $10^3$ to $10^4$ lower titers at 39.1° C. than at 34.5° C.

Rationale for Multiple Plaque-Purifications

Virus titrations are performed by infecting dishes (or tubes) of cells with serial, ten-fold dilutions of the virus to be assayed. An area of cellular destruction (or plaque) can be recognized microscopically, or with vital stains (e.g., neutral red). Dishes containing a million cells that are infected with 100 and 10 infectious virus particles, respectively, will show 100 and 10 areas of destruction (or plaques) and are said to be infected with 100 or 10 plaque-forming units (PFU) of virus. If a bottle has $10^8$ PFU/ml of virus and a dish is infected with 0.1 ml of a $10^{-6}$ dilution of virus, 10 areas of destruction (or plaques) will be seen. Each plaque consists of the progeny of one virus particle. Plaques are colonies of "identical" virus particles. Therefore, the most effective way to purify a virus is to plaque-purify repeatedly.

Establishing Working TK⁻tr BHV-1 Pools

To be useful to confer resistance upon animals to BHV-1 infections, the TK⁻tr BHV-1 mutants must be maintained in a viable form. Propagation of mutants obtained by the above method in RAB-9 cells in culture was selected as the method of producing working pools of viable TK⁻tr BHV-1. The pools were stored at -70° C. in APMEM plus 10% lamb serum. From these pools TK⁻tr BHV-1 was drawn for further testing or experimentation and for administration to cattle to induce resistance to BHV-1 infection.

Characterization of the Produced TK⁻tr Mutants

Restriction nuclease analyses are useful for the identification of herpesviruses and for differentiating closely related herpesvirus strains. Hayward, et al. *Anatomy of Herpes Simplex Virus DNA: Strain Differences and Heterogeneity in Locations of Restriction Endonuclease Cleavage Sites,* Proc. Nat. Acad. Sci. U.S.A. 1768-72 (1975). For example, herpes simplex virus type 1 can be distinguished from herpes simplex virus type 2 on the basis of their restriction nuclease patterns. Differences between infectious bovine rhinotracheitis and infectious pustular vulvovaginitis strains of BHV-1 have also been detected by comparing their restriction nuclease patterns. Engels, et al, *Comparison of the Genomes of Infectious Bovine Rhinotracheitis (IBR) and Infectious Pustular Vulvovaginitis (IPV), Virus Strains by Restriction Endonuclease Analyses,* Arch. Virol. 67, 169-74 (1981). Restriction endonuclease analyses showed that the BHV-1 strains utilized in producing the TK⁻ mutants were authentic infectious bovine rhinotracheitis virus strains. Restriction nuclease analyses also provided confirmation that the TK⁻tr BHV-1 mutants were authentic BHV-1 strains derived from parental TK⁺ BHV-1 (Los Angeles Strain).

To be certain that the produced mutants lacked the ability to induce thymidine kinase activity in infected cells, the thymidine kinase activity of cells infected by wild-type BHV-1 was compared to cells infected by the produced mutant. The data obtained are set forth below:

INDUCTION OF THYMIDINE KINASE ACTIVITY BY WILD-TYPE TK⁺ BHV-1 STRAINS AND BY TK⁻tr BHV-1 MUTANTS IN BOVINE EMBRYO TRACHEAL (EBTr) AND RABBIT SKIN (RAB-9) CELLS

| Expt | Conditions[a] | Thymidine kinase activity[b] |
|---|---|---|
| 1 | Mock-infected EBTr | 0.5 |
| | wt BHV-1(LA)-infected EBTr | 4.1 |
| | wt BHV-1(Cooper)-infected EBTr | 5.2 |
| 2 | Mock-infected RAB-9 | 2.9 |
| | wt BHV-1(LA)-infected RAB-9 | 5.7 |
| | wt BHV-1(Cooper)-infected RAB-9 | 6.5 |
| 3 | Mock-infected RAB-9 | 3.1 |
| | wt BHV-1(LA)-infected RAB-9 | 6.6 |
| | Mock-infected RAB(BU) | 0.1 |
| | wt BHV-1(LA)-infected RAB(BU) | 8.3 |
| 4 | Mock-infected RAB-9 | 0.25 |
| | wt BHV-1(LA)-infected RAB-9 | 10.76 |
| | Mutant BHV-1(B8-C)-infected RAB-9 | 0.23 |
| | Mutant BHV-1(B8-D)-infected RAB-9 | 0.25 |
| 5 | Mock-infected RAB-9 | 1.4 |
| | wt BHV-1(LA)-infected RAB-9 | 3.8 |
| | Mutant BHV-1(B8-D)-infected RAB-9 | 1.1 |
| 6 | Mock-infected RAB(BU) | 0.04 |
| | wt BHV-1(Cooper)-infected RAB(BU) | 3.1 |
| | Mutant BHV-1(B8-D53)-infected RAB(BU) | 0.02 |

[a]Subconfluent (Expts 2, 3, 5, and 6) or stationary phase (Expts 1 and 4) cultures were infected at 36.5° with 3-10 PFU/cell of wild-type (wt) TK⁺ BHV-1 or TK⁻ BHV-1 mutants. Enzyme extracts were prepared at 6 hrafter infection and assayed for TK activity for 10 min at 38° with ³H-dThd and ATP as substrates.
[b]TK activity expressed as picomoles dTMP formed in 10 min at 38° per ug protein.

The results clearly show that the TK⁻tr BHV-1 mutants lacked the ability to induce a virus encoded thymidine kinase activity in either TK⁺ or TK⁻ cells. In contrast, the wild-type BHV-1 increased cell associated thymidine kinase activity approximately 40 fold due to the formation of a virus encoded enzyme in the infected cells. Thus, these data clearly demonstrate that the desired thymidine kinase negative mutant was produced by the method employed.

Use of TK⁻tr BHV-1 to Induce Resistance to BHV-1 Infection

Experiments to evaluate the efficacy of TK⁻tr BHV-1 containing vaccine in conferring resistance to BHV-1 infections have been carried out. The vaccines were prepared by adding TK⁻tr BHV-1 to a vehicle suitable for the route of administration to be utilized. To date, intranasally and intravenously administered vaccine has proved effective in inducing resistance to infectious bovine rhinotracheitis. It is anticipated that this vaccine administered by other routes such as enteral and parenteral would also be effective. The effective vaccinal dose range in calves is $10^6$ to $10^8$ PFU.

EXAMPLE 1

In the initial trial, two Holstein calves were vaccinated by intranasal administration of $5 \times 10^6$ PFU TK⁻tr BHV-1. Two other calves were untreated and kept as contact controls. Vaccinated calves did not show any signs of active disease. Assays of vaccinated calves' nasal secretions were conducted to be certain that viable virus had been administered. The results of these assays were as follows:

ISOLATION OF BHV-1 FROM NASAL SWABS OF CALVES VACCINATED WITH TK⁻tr BHV-1 (B8-D) MUTANT AND SUBSEQUENTLY CHALLENGED WITH BHV-1 (COOPER)

| Calf No. | Days after TK⁻ BHV-1 exposure | | | | | | | | | | Days after BHV-1 (Cooper) challenge | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 | 7 | 8 | 9 | 10 |
| 45 | +* | + | + | + | + | + | + | + | + | + | − | + | + | − | + | + | − | + | − | − |
| 46 | − | − | − | + | − | + | − | − | − | − | − | + | + | + | + | + | + | + | + | + |
| 47 | − | − | − | − | − | − | − | − | − | − | − | + | + | + | + | + | + | + | + | + |
| 48 | + | + | + | + | + | + | + | + | + | − | − | + | + | + | + | + | + | − | − | − |

\* − signifies BHV-1 isolated; − signifies virus not isolated from nasal swabs, even after 3 blind passages in bovine turbinate cells.
Calves #46, 47 were untreated controls
Calves #45, 48 were vaccinated with TK⁻tr BHV-1

As demonstrated by these data, virus was found for nine to ten days in the nasal secretions of vaccinated calves, but the amount of virus found decreased significantly on days eight to ten. The finding of virus in nasal secretions demonstrates that the TK⁻tr BHV-1 employed was viable and replicated at the site of administration.

To determine if the vaccine had successfully induced resistance to infection, control and vaccinated calves were exposed to virulent virus forty-two days following vaccination. Control calves showed the expected symptoms of infectious bovine rhinotracheitis (high fever, serous nasal discharge, depression of white blood cell counts), but TK⁻tr BHV-1 vaccinated animals showed no signs of active disease. Additional evidence supporting the efficacy of the TK⁻tr BHV-1 vaccine was provided by finding BHV-1 specific neutralizing antibodies in the serum of one of the vaccinated calves. Prior to vaccination, each of the calves had no specific BHV-1 antibodies in its sera. Therefore, administration of TK⁻tr BHV-1 containing vaccine was effective in stimulating production of antibody specific to BHV-1.

The vaccinated animals were also tested to determine if the TK⁻tr BHV-1 containing vaccine had induced reactivatable latent virus infections. Seventy-seven days after vaccination, all of the calves were euthanized and central nervous system tissues were collected and prepared for examination. Virus was not recovered from the examined tissues of either vaccinated or controlled calves. Therefore, the mutant containing vaccine had effectively induced resistance to infectious bovine rhinotracheitis without producing latent virus infections where the virus was recoverable by standard procedures.

It was important to establish that the mutant BHV-1 was stable and would not readily revert in the calf to the TK⁺ phenotype. In this series of experiments, control calf No. 46 became infected with TK⁻tr BHV-1 by contact with its penmate. The above table shows that BHV-1 was isolated from this calf on days 4 and 6 after calves Nos. 45 and 48 were vaccinated with TK⁻tr BHV-1. The infection was, however, asymptomatic. The virus samples isolated in nasal swabs of calf No. 46 on days 4 and 6 were analyzed for TK⁻inducing activity. These experiments showed that the viruses isolated from calf No. 46 had the TK⁻ phenotype. Similarly, the viruses isolated from calves Nos. 45 and 48 on the first and last days of shedding were assayed. These viruses also had the TK⁻ phenotype. The results clearly show that the TK⁻virus used as a vaccine did not revert to the TK⁺ phenotype in the vaccinated calves or after natural transmission to calf No. 46.

EXAMPLE 2

In the second trial twenty calves were used. The vaccinal dose utilized was $2 \times 10^7$ PFU of TK⁻BHV-1. Six calves received the vaccine intranasally; four calves received the vaccine intravenously. The ten remaining calves were untreated and served as controls. The vaccinated calves were initially examined to determine if virus replication had occurred at the site of vaccination. Virus was isolated from nasal swabs of intranasally vaccinated calves and from blood samples of intravenously vaccinated calves. These findings indicated that viral replications had occurred and thus, viable virus had been administered.

The calves were monitored for signs of vaccine caused acute viral illness. The intranasally vaccinated calves were separated into two pens. The three calves in one of the pens exhibited no signs of viral infection. The three calves in the other pen became febrile on days 5, 6 and 7 following vaccination and exhibited nasal exudates, some lung involvement, and an elevated total white cell count. However, these clinical signs did not suggest viral infection, but rather were indicative of bacterial infection since three of the non-vaccinated control calves had similar symptoms. The intravenously vaccinated calves also did not demonstrate signs of acute viral infection. Forty-two days following vaccination, control and vaccinated calves were challenged with virulent virus to determine the efficacy of the vaccine in producing resistance to infection. Each of the control calves exhibited clinical signs of active viral disease. In marked contrast, the intranasally vaccinated calves and the intravenously vaccinated calves exhibited none of the signs indicative of active viral disease.

To investigate whether recrudescence of infectious bovine rhinotracheitis occurred after stress, vaccinated calves were treated with dexamethasone (0.1 mg/kg body weight) 30 days after the administration of the challenging BHV-1. Dexamethasone induced stress did not lead to recrudescence of disease.

These examples demonstrate that TK⁻tr BHV-1 is useful as a safe and effective vaccine against infectious bovine rhinotracheitis. Intravenous and intranasal vaccination fully protected animals exposed to virulent virus from developing infectious bovine rhinotracheitis. Yet, the vaccine virus replicates only to a limited extent at the site of innoculation and does not cause active disease. Additionally, vaccine administration did not induce recurrent herpes infections and did not produce disease when transmitted to non-vaccinated penmates. Vaccine virus did not revert to virulence or to the wild TK− phenotype in vaccinated calves or in non-vaccinated calves after natural transmission from vaccinated calves.

The present invention, therefore, is well-suited and adapted to attain the objects and ends and has the advantages and features mentioned, as well as others inherent therein.

While the presently preferred embodiments of the invention have been set forth for purposes of disclosure, changes and modifications therein can be made which are within the spirit of the invention as defined by the scope of the appended claims.

What is claimed is:

1. A temperature-resistant bovine herpesvirus-1 which fails to produce any functional thymidine kinase as a result of mutagen-induced mutation.

2. The temperature-resistant bovine herpesvirus-1 as claimed in claim 1, wherein said virus has the identifying characteristics of ATCC No. VR-2066.

3. A temperature-resistant bovine herpesvirus-1 which fails to produce any functional thymidine kinase as a result of mutagen-induced mutation produced by a process comprising:
   (A) propagating thymidine kinase-positive bovine herpesvirus-1 in thymidine kinase-positive cells at about 34.5° C. in the presence of a mutagen and selecting for thymidine kniase-negative bovine herpesvirus-1;
   (B) plaque-purifiying the resulting thymidine kinase-negative bovine herpesvirus-1 so as to obtain bovine herpesvirus-1 mutants which fail to produce any functional thymidine kinase; and
   (C) propragating the resulting plaque-purified thymidine kinase-negative bovine herpesvirus-1 mutants in thymidine kinase-positive cells at about 39.1° C. and selecting for temperature-resistant bovine herpesvirus-1 mutants which fail to produce any functional thymidine kinase.

4. The temperature-resistant bovine herpesvirus-1 as claimed in claim 3, wherein said mutagen is 5-bromodeoxyuridine.

5. A modified-live virus vaccine for infectious bovine rhinotracheitis comprising:
   (A) a pharmaceutically effective amount of a temperature-resistant bovine herpesvirus-1 which fails to produce any functional thymidine kinase as a result of mutagen-induced mutation; and
   (B) a pharmaceutically acceptable carrier or diluent.

6. The modified-live virus vaccine as claimed in claim 5, wherein said virus has the identifying characteristics of ATCC No. VR-2066.

7. The modified-live virus vaccine as claimed in claim 5, wherein said pharmaceutical effective amount is about $10^6$ to $10^8$ PFU.

8. A modified-live virus vaccine for infectious bovine rhinotracheitis comprising:
   (A) a pharmaceutically effective amount of a temperature-resistant bovine herpesvirus-1 which fails to produce any functional thymidine kinase as a result of mutagen-induced mutation prepared by the process comprising:
      (1) propagating thymidine kinase-positive bovine herpesvirus-1 in thymidine kinase-positive cells at about 34.5° C. in the presence of a mutagen and selecting for thymidine kinase-negative bovine herpesvirus-1;
      (2) plaque-purifying the resulting thymidine kinase-negative bovine herpesvirus-1 so as to obtain bovine herpesvirus-1 mutants which fails to produce any functional thymidine kinase; and
      (3) propagating the resulting plaque-purified thymidine kinase-negative bovine herpesvirus-1 mutants in thymidine kinase-positive cells at about 39.1° C. and selecting for temperature-resistant bovine herpesvirus-1 mutants which fail to produce any functional thymidine kinase.
   (B) a pharmaceutically acceptable carrier or diluent.

9. The modified-live virus vaccine as claimed in claim 8, wherein said mutagen is 5-bromodeoxyuridine.

10. The modified-live virus vaccine as claimed in claim 8, wherein said pharmaceutical effective amount is about $10^6$ to $10^8$ PFU.

11. A method of immunizing an animal against infectious bovine rhinotracheitis comprising administering a pharmaceutically effective amount of a temperature-resistant bovine herpesvirus-1 which fails to produce any functional thymidine kinase as a result of mutagen-induced mutation, prepared by the process comprising:
   (1) propagating thymidine kinase-positive bovine herpesvirus-1 in thymidine kinase-positive cells at about 34.5° C. in the presence of a mutagen and selecting for thymidine kinase-negative bovine herpesvirus-1;
   (2) plaque-purifying the resulting thymidine kinase-negative bovine herpesvirus-1 so as obtain bovine herpesvirus-1 mutants which fail to produce any functional thymidine kinase; and
   (3) propagating the resulting plaque-purified thymidine kinase-negative bovine herpes-virus-1 mutants in thymidine kinase-positive cells at about 39.1° C. and selecting for temperature-resistant bovine herpes-virus-1 mutants which fail to produce any functional thymidine kinase to an animal.

12. The method as claimed in claim 11, wherein said virus has the identifying characteristics of ATCC No. VR-2066.

13. The method as claimed in claim 11, wherein said mutagen is 5-bromodeoxyuridine.

14. The method as claimed in claim 11, wherein said administering is conducted intranasally or parenterally.

15. The method as claimed in claim 11, wherein said animal is selected from the group consisting of bovine, goats and swine.

16. The method of claim 15, wherein said animal is bovine.

17. The method of claim 11, wherein said pharmaceutically effective amount is $10^6$ to $10^8$ PFU.

* * * * *